(12) United States Patent
Ueda et al.

(10) Patent No.: US 11,172,942 B2
(45) Date of Patent: Nov. 16, 2021

(54) ARTHROSCOPIC SURGERY METHOD FOR ANKLE LIGAMENT RECONSTRUCTION

(71) Applicant: OLYMPUS CORPORATION, Hachioji (JP)

(72) Inventors: Sohei Ueda, Tokyo (JP); Chie Onuma, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 266 days.

(21) Appl. No.: 16/257,680

(22) Filed: Jan. 25, 2019

(65) Prior Publication Data

US 2019/0150972 A1    May 23, 2019

Related U.S. Application Data

(63) Continuation of application No. 15/084,975, filed on Mar. 30, 2016, now Pat. No. 10,213,223.

(60) Provisional application No. 62/269,455, filed on Dec. 18, 2015.

(51) Int. Cl.
*A61B 17/32* (2006.01)
*A61B 17/16* (2006.01)
*A61B 17/56* (2006.01)

(52) U.S. Cl.
CPC .. *A61B 17/1682* (2013.01); *A61B 17/320068* (2013.01); *A61B 17/1604* (2013.01); *A61B 2017/320069* (2017.08); *A61B 2017/320073* (2017.08); *A61B 2017/564* (2013.01)

(58) Field of Classification Search
CPC .............................................. A61B 17/320068
See application file for complete search history.

(56) References Cited

U.S. PATENT DOCUMENTS

| | | | | |
|---|---|---|---|---|
| 1,185,380 A * | 5/1916 | Davis | ................... | B27G 15/00 408/205 |
| 3,494,628 A * | 2/1970 | Spademan | ............... | A63C 9/08 280/624 |
| 5,092,719 A * | 3/1992 | Zsiger | ................... | B27G 15/00 408/213 |
| 5,312,207 A * | 5/1994 | Pomp | ..................... | B23P 15/32 408/212 |
| 5,350,380 A * | 9/1994 | Goble | ................ | A61B 17/1714 606/102 |
| 5,489,310 A * | 2/1996 | Mikhail | ............. | A61B 17/1684 623/19.11 |
| 6,558,389 B2 * | 5/2003 | Clark | ................... | A61F 2/0805 606/232 |
| 7,270,666 B2 * | 9/2007 | Lombardo | ......... | A61B 17/1714 606/308 |
| 7,637,949 B2 * | 12/2009 | Hart | ..................... | A61B 17/686 606/305 |
| 8,727,679 B2 * | 5/2014 | Evatt | ..................... | B27G 15/00 408/211 |

(Continued)

OTHER PUBLICATIONS

May 23, 2018 Office Action issued in U.S. Appl. No. 15/084,975.

*Primary Examiner* — Zade Coley
(74) *Attorney, Agent, or Firm* — Oliff PLC

(57) ABSTRACT

An arthroscopic surgery method for ankle ligament reconstruction of this embodiment is removed using an ultrasonic treatment tool, blowing away a synovial membrane, and secures the view for a remnant ligament. Then, bone holes are produced to a fibula, a talus and a calcaneus using the ultrasonic treatment tool.

5 Claims, 13 Drawing Sheets

(56) References Cited

U.S. PATENT DOCUMENTS

| | | | | |
|---|---|---|---|---|
| 8,974,458 B2* | 3/2015 | Long | ................... | A61F 2/4684 |
| | | | | 606/80 |
| 2002/0141838 A1* | 10/2002 | Thomas | ................ | B27G 15/00 |
| | | | | 408/214 |
| 2006/0253050 A1* | 11/2006 | Yoshimine | ........ | A61H 23/0245 |
| | | | | 601/2 |
| 2007/0038302 A1* | 2/2007 | Shultz | ................ | A61B 17/1684 |
| | | | | 623/19.11 |
| 2007/0275348 A1* | 11/2007 | Lemon | .................... | A61C 3/03 |
| | | | | 433/119 |
| 2008/0234711 A1* | 9/2008 | Houser | .......... | A61B 17/320068 |
| | | | | 606/169 |
| 2009/0018654 A1* | 1/2009 | Schmieding | ....... | A61B 17/1675 |
| | | | | 623/13.14 |
| 2009/0105840 A1* | 4/2009 | Reiley | .................. | A61F 2/4202 |
| | | | | 623/21.18 |
| 2013/0090662 A1* | 4/2013 | Hanson | ............. | A61B 17/8805 |
| | | | | 606/96 |
| 2013/0134632 A1* | 5/2013 | Snedeker | .................. | A61F 2/08 |
| | | | | 264/320 |
| 2015/0150570 A1* | 6/2015 | Okuno | ................. | A61B 17/1764 |
| | | | | 606/87 |
| 2017/0100156 A1* | 4/2017 | Ueda | ................. | A61B 17/3205 |

* cited by examiner

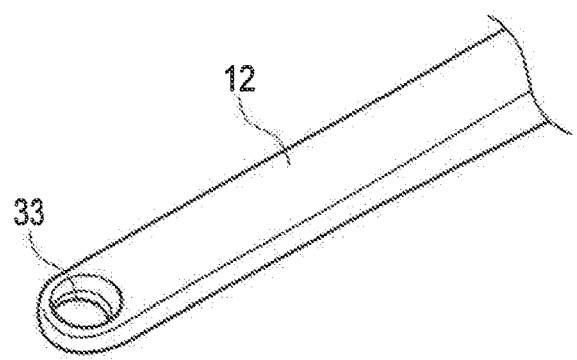
F I G. 4
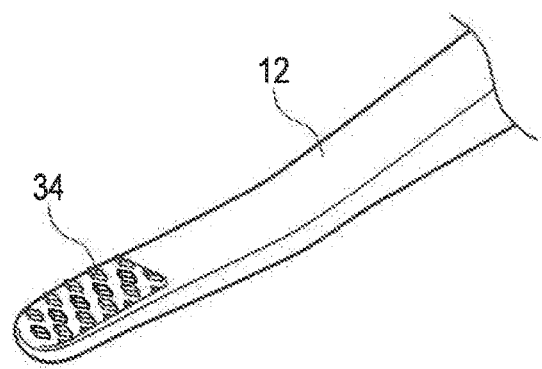
F I G. 5A
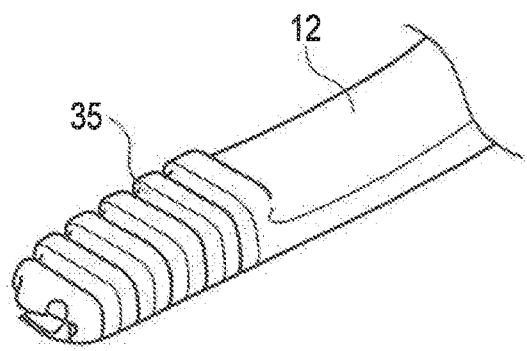
F I G. 5B

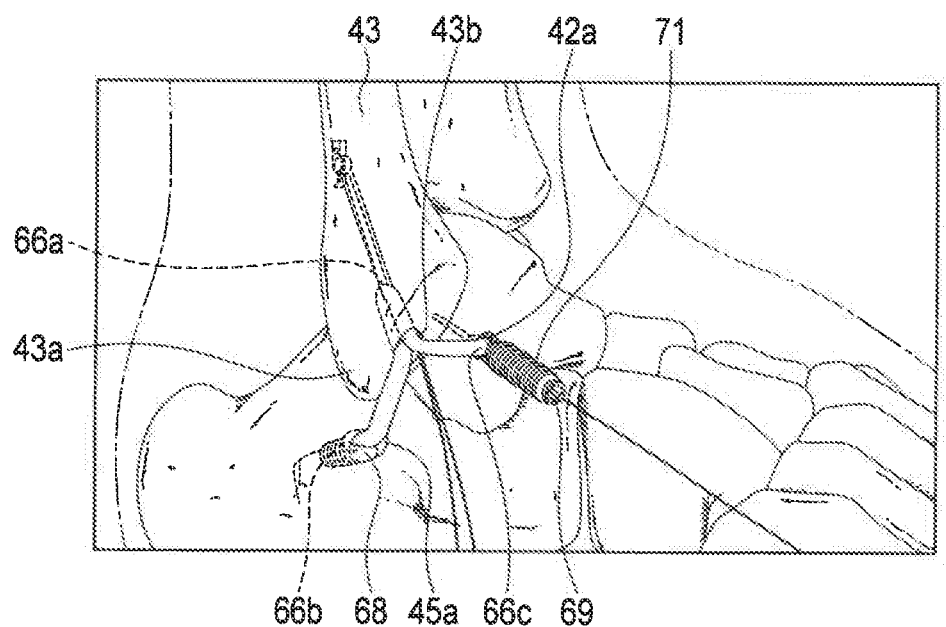
F I G. 21

ARTHROSCOPIC SURGERY METHOD FOR ANKLE LIGAMENT RECONSTRUCTION

CROSS-REFERENCE TO RELATED APPLICATIONS

This application is a Continuation of U.S. application Ser. No. 15/084,975 filed Mar. 30, 2016, which is based upon and claims the benefit of prior U.S. Provisional Application No. 62/269,455 filed Dec. 18, 2015, the entire contents of which are incorporated herein by reference.

BACKGROUND OF THE INVENTION

1. Field of the Invention

The present invention relates to an arthroscopic surgery method for ankle ligament reconstruction which an ultrasonic treatment tool is used.

2. Description of the Related Art

Generally in an arthroscopic surgical operation, two or three portals of small holes are made around a joint (in a skin surface), and an arthroscope comprising a hard mirror and a medical treatment tool are inserted through these portals. Further, in a state where perfusate such as saline is filled into the joint, the surgical operation is carried out while confirming an image reflected in a monitor.

As conventional medical treatment tools, there are known a tool such as a drill that is rotated to make a bone hole and a shaver system that is pressed against a bone to shave off the bone. Additionally, an ablator or the like is also used which utilizes a radiofrequency (RF) system to stop ablation bleeding.

In the arthroscopic surgical operation in which such a conventional medical treatment tool is used, there are problems to be concerned about in several treatments. For example, when the drill or the like is used in making the bone hole, the hole is made only in a travelling direction of a drill blade, and hence in a case where the bone hole is made in the joint, an introducing direction is restricted by a position of a treatment target region. Furthermore, when a tip portion of the drill is vibrated and moved at the start of the making of the bone hole, an unnecessarily shaved region is generated, and hence it is necessary to sufficiently carefully use the drill. Additionally, a treatment tool using a rotary blade is moved while mechanically rotating the blade to shave the bone, whereby unevenness remains in a treated surface and it is not easy to smoothen the surface. Additionally, when a cartilage or the bone is shaved off by using a treatment tool that is manually operated, an amount of the cartilage or the like to be shaved off varies with a force to be given to the treatment tool, and hence the force has to be delicately adjusted, which requires time and labor. Furthermore, a treatment tool using a radiofrequency might cause thermal damages to a tissue of a treatment target.

BRIEF SUMMARY OF THE INVENTION

According to an embodiment of the present invention, there is provided an arthroscopic surgery method for ankle ligament reconstruction comprising: a removing step of cutting and removing removal target regions comprising at least a synovial membrane, a synovium-related adipose tissue and a persistence ligament by a side surface of a treating portion of an ultrasonic treatment tool that generates ultrasonic vibration; a bone hole forming step of hitting, against each of a fibula, a talus and a calcaneus, a tip of the treating portion of the ultrasonic treatment tool used in the removing step, whereby bone holes to fix tendons are formed in the fibula, the talus and the calcaneus, respectively.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a view showing an example of a curette to be disposed in the probe:

FIG. 5A is a view showing an example of a twill line to treating portion of the probe;

FIG. 5B is a view showing an example of a straight knurl treating portion of the probe;

FIG. 21 is a view showing a surgical operation step of fixing the tendon into the talus bone hole with a screw.

DETAILED DESCRIPTION OF THE PREFERRED EMBODIMENT

Hereinafter, with reference to the drawings, there will be described an arthroscopic surgery method for ankle ligament reconstruction in which there is used an ultrasonic treatment tool according to an embodiment of the present invention. The present embodiment is the arthroscopic surgery method for ankle ligament reconstruction in which the ultrasonic treatment tool is used for treatments to remove a synovial membrane/a soft tissue and to secure a viewing field, and for the formation of a bone hole in a fibula, the formation of a bone hole in a talus, and the formation of a bone hole in a calcaneus.

Figure 1:
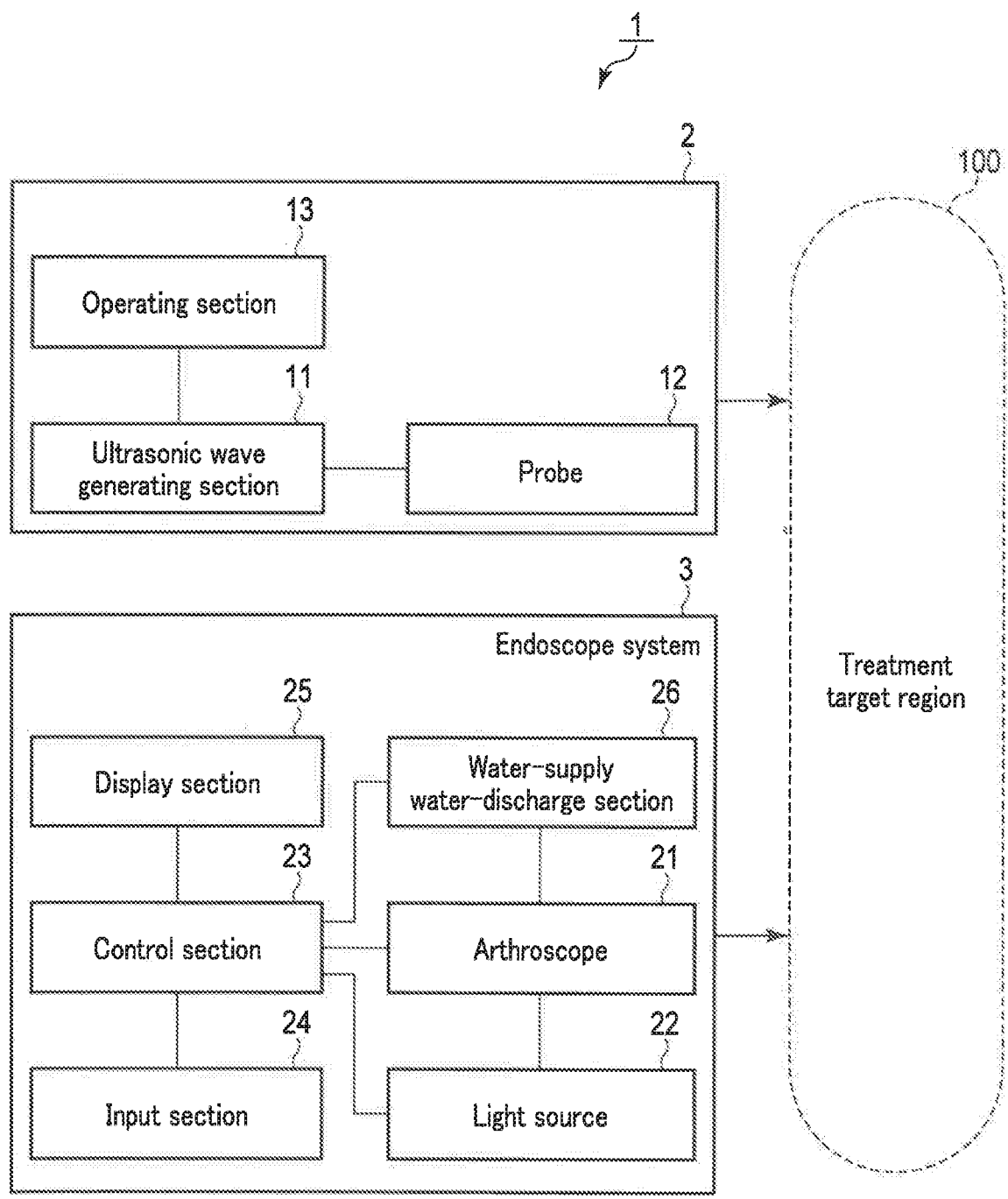
FIG. 1 is a diagram showing a constitution example of a surgical system comprising an ultrasonic treatment tool to carry out an arthroscopic surgery method for ankle ligament reconstruction of one embodiment.
Figure 2:
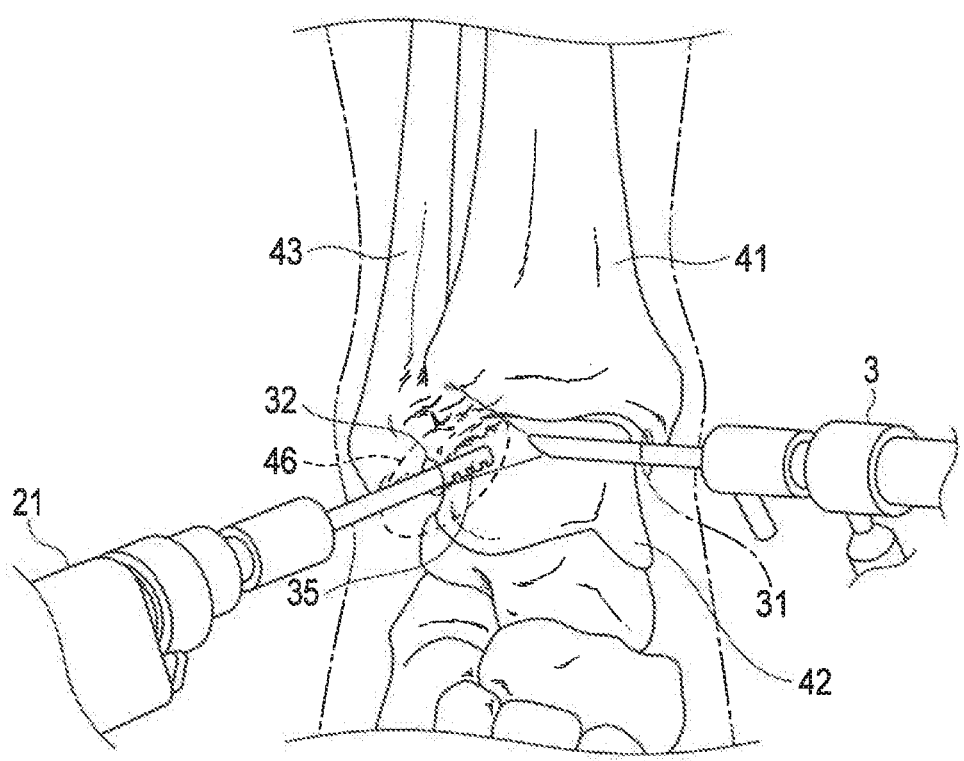
FIG. 2 is a view conceptually showing a step of removing a synovial membrane/a soft tissue or the like by an arthroscope and the ultrasonic treatment tool inserted into a joint.

FIG. 1 shows a constitution example of a surgical system comprising the ultrasonic treatment of to carry out the arthroscopic surgery method for ankle ligament reconstruction of the present embodiment. FIG. 2 is a view conceptually snowing a situation of a surgical operation by an arthroscope and the ultrasonic treatment tool inserted into a joint. Hereinafter, in the present embodiment, an ankle ligament will be described as one example of a treatment target region 100 but the region is not limited to this ligament, and it is possible to easily carry out a surgical operation in another ligament similarly by use of the ultrasonic treatment tool.

A surgical system 1 of the present embodiment is constituted of an ultrasonic treatment tool 2 and an endoscope system 3 including an arthroscope 21. As shown in FIG. 2, portals 31 and 32 are prepared on a front inner side and a front outer side, the arthroscope 21 is inserted from one of the portals, and a probe 12 of the ultrasonic treatment tool 2, a surgical instrument or the like is inserted from the other portal.

The ultrasonic treatment tool 2 comprises an ultrasonic wave generating section 11 that generates ultrasonic vibration by an ultrasonic vibration element (e.g., a piezoelectric element), the probe 12 that transmits the ultrasonic vibration to perform a cutting treatment of the treatment target region, and an operating section 13 that drives and controls the ultrasonic wave generating section 11 to perform an on/off operation of the generation of the ultrasonic vibration.

Hereinafter, a treating portion of the probe 12 of the ultrasonic treatment tool 2 will be described.

The probe 12 for use in the present embodiment is a thin and long rod-like member linearly extending in a longitudinal axis direction and having a diameter of about 2 mm to 4 mm, and has a to distal portion and a proximal portion. The proximal portion is coupled with the ultrasonic wave generating section 11, and in the distal portion, an after-mentioned treating portion is disposed.

Figure 3A:
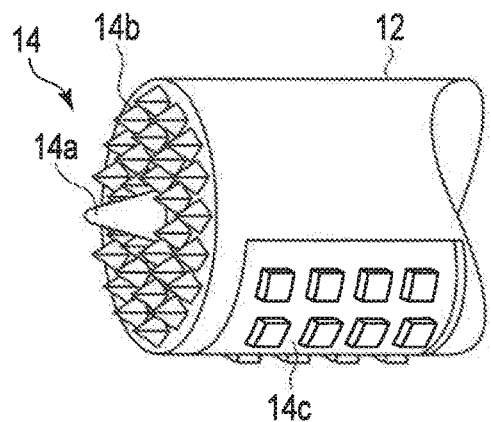
FIG. 3A is a view showing a constitution example where a tip of a treating portion of a probe is round.

In the probe 12 shown in FIG. 3A, a treating portion 14 to form a bone hole in a bone is disposed. In a center of a distal surface of the treating portion 14, a pointed projection 14a longer than any ether portion is disposed to be positioned with a precedingly formed guide hole, and around the pointed projection, a plurality of projections 14b are disposed. Additionally, rectangular projecting portions 14c are disposed on a side surface of the treating portion 14 and formed into a checkered pattern along about a half of this peripheral surface. It is to be noted that the plurality projections 14b are disposed to improve a cutting efficiency, and are not essentially required, and the bone hole may be formed by a shape of a tip of the treating portion in which any projections are not disposed.

In the present embodiment, the probe 12 transmits the ultrasonic vibration to the treating portion 14 and the treating portion 14 performs the cutting treatment to form the bone holes in a talus 42, a fibula 43 and a calcaneus 45. Needless to say, the pointed projection 14a is utilized in a case where the guide hole is beforehand formed, and therefore is not an essentially required portion, and the treating portion may be constituted only of the projections 14b.

The ultrasonic treatment tool 2 enables the cutting treatment to bones such as a cartilage and a subchondral bone (a cortical bone and a cancellous bone) and all regions of a biological tissue. That is, the cartilage can be melted and cut off by frictional heat generated between the treating portion 14 and the cartilage, when the projecting portions 14c comprising edges formed on the side surface of the probe 12 are hit against the cartilage. Additionally, the bone can be cut by hammering the bone with the projections 14b of the treating portion 14 disposed at the tip of the probe 12 by use of the ultrasonic vibration and very finely grinding and cutting the bone. Therefore, when the treating portion of the probe tip is formed into a shape corresponding to a cutting target, not only a type of cutting target region but also an amount of the region to be cut and a shape of the region can suitably be selected. It is to be noted that an amount of the bone to be cut by the projecting portions 14c disposed on the side surface of the probe 12 smaller than an amount of the bone to be cut by the projections 14b, but the projecting portions 14c can also hammer and cut the bone.

Figure 3B:
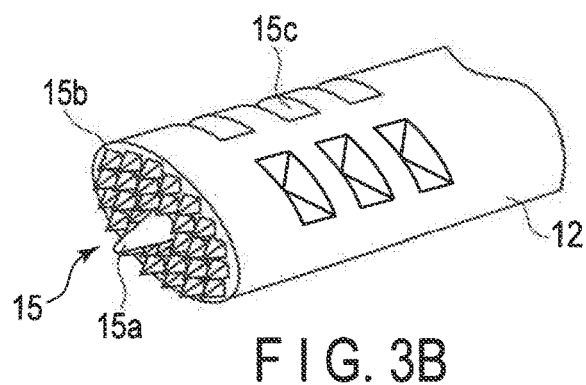
FIG. 3B is a view showing a example where the tip of the treating portion of the probe is elliptic.
Figure 3C:
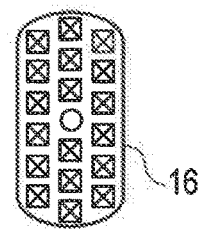
FIG. 3C is a view showing an example where the tip of the treating portion of the probe has a long hole shape.
Figure 3D:
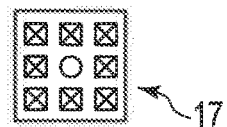
FIG. 3D is a view showing an example where the tip of the treating portion of the probe is rectangular.

Additionally, a conventional drill used in forming the bone hole is rotated to make the hole, and hence the hole is basically round, and even when the drill is horizontally swung, a diameter of the hole only increases in an undetermined manner, and the hole cannot be formed into a desirable shape. On the other hand, the probe of the ultrasonic treatment tool 2 does not rotate but minutely moves forward and backward, and hence when the probe tip abuts on the surface of the bone to vertically hammer the surface during the cutting, the shape of the bone hole is not limited to the round shape, and the bone hole can be formed into a shape in accordance with an outer shape of the treating portion (or a sectional shape of the probe). The bone hole of an optional shape can be formed by moving region on which the treating portion 14 abuts. In a case where the shape of the bone hole to be formed is determined, for example, when a treating portion 15 including one pointed projection 15a and a plurality of projections 15b is formed at a tip of an elliptic probe 12 as shown in FIG. 3B, an elliptic bone hole can be formed. In this example, in a side surface of the probe 12, two rows of grooves 15c are arranged in a longitudinal axis direction to constitute a cutting edge. Similarly, also by a long hole (track-shaped) treating portion 16 shown in FIG. 3C or a rectangular treating portion 17 shown in FIG. 3D, a bone hole of a shape in accordance with a shape of the treating portion is formed.

In the ultrasonic tool, the cutting is performed by the minute vibration, and hence more precise processing is enabled. First, a small bone hole (a first bone hole) is precedingly formed, and additionally, the bone is cut to form the hole into a desirable larger shape, which makes it possible to form a bone hole (a second bone ole) of an optional shape.

Furthermore, the bone hole is not limited to a linear shape, but it is also possible to form a bone hole having a curved region. For example, when the bone has a linear shape, a length (a depth) of the bone hole is only short, but when there occurs the problem that a tendon cannot be fixed to this bone hole, the tendon can be fixed by forming a curved bone hole. The bone hole having the curved region can be achieved by using a probe having a bend in its distal portion.

Also as to the diameter or a width of the bone hole, there can be formed not only a hole of the same diameter or a hole of the same width but also a hole of a tapered shape having the diameter or the width that decreases from its inlet. In this case, the bone hole can be formed into each of a tapered shape having a stepped region and a tapered shape in which any stepped regions are not disposed. Furthermore, a bone hole can be formed into such a shape that the width or the diameter of the inlet is small and the diameter or the width increases in a deeper region. This may be achieved by using, for example, an L-shaped treating portion having a bent tip. It is to be noted that by a treatment tool in which a conventional drill is used, the linear bone hole of the same diameter can be formed, or by replacing its drill blade with a drill blade having a different diameter, the bone hole can be formed into a tapered shape having a stepped region and having a diameter that gradually decreases from an inlet.

In the present embodiment, a bone hole to be utilized in the reconstruction can be formed into a shape corresponding to a sectional shape of the tendon (the ligament) removed from another region at once. Additionally, the treating portion may be prepared into a shape equal to the sectional shape of the tendon in advance.

It is to be noted that when the probe tip having an edge is horizontally pressed against the surface of the bone, a treatment surface of the treatment target region is frictionally hammered while vibrating, and hence the region can be resected by the hammering and cutting-off with the edge of the probe tip. It is to be noted that a treatment target region having an elasticity, e.g., the cartilage, fat or the like can be resented by cutting-off with the edge and melting by frictional heat.

Another treating portion of the probe 12 for use in the present embodiment will be described.

A curette 33 disposed at a tip of a probe 12 shown in FIG. 4 is provided with a round hole, and a cartilage, a bone or the like can be cut with an edge of the hole while ultrasonically vibrating.

Additionally, a twill line treating portion 34 disposed at a distal of a probe 12 shown in FIG. 5A is provided with a plurality of rhombic projecting portions, a cartilage is cut off with edges of the projecting portions while ultrasonically vibrating, and a bone is hammered and cut with edge tip surfaces of the projecting portions.

A straight knurl treating portion 35 disposed at a tip of a probe 12 shown in FIG. 5B is provided with edges formed by a plurality of grooves arranged in parallel, a cartilage is melted by friction on tip surfaces of the ultrasonically vibrating and cut off with the edges, and further a bone hammered and cut with the tip surfaces of the edges.

In the ultrasonic treatment tool 2, mechanical cutting by minute sliding is performed by giving the ultrasonic vibration to the probe having one end supported by the ultrasonic transducer, and hence an amount of a treatment region to be cut off can be adjusted in accordance with a degree of a strength at which the treating portion 14 of its tip is pressed against the treatment region. That is, when the treating portion lightly comes in contact with the region, the amount of the region to be cut off decreases, but when flattening of the surface of the treatment target region and minute cutting-off are achieved and the treating portion is strongly brought into contact with the region, the amount of the region to be cut off increases. Therefore, a cutting degree by an operator can be adjusted, and efficient cutting, resecting or the like can be achieved.

The endoscope system 3 is constituted of the arthroscope 21 comprising a hard mirror that is one type of endoscope, a visible light source 22 that is a light source of illumination light for irradiation with the illumination light of visible light, a control section 23 that controls the whole endoscope system 3, an input section 24 such as a keyboard or a touch panel, a display section 25 that displays surgical operation information including a photographed surgical operation situation, and a water-supply water-discharge section 26 that supplies, discharges or circulates perfusate such as saline in a periphery including the ankle ligament of the treatment target region 100.

In the present embodiment, the water-supply water-discharge section 26 supplies the saline to the treatment region through the arthroscopy 21 and discharges the saline from the region through the arthroscope, but the saline may be supplied and discharged by the ultrasonic treatment tool 2.

Figure 6:
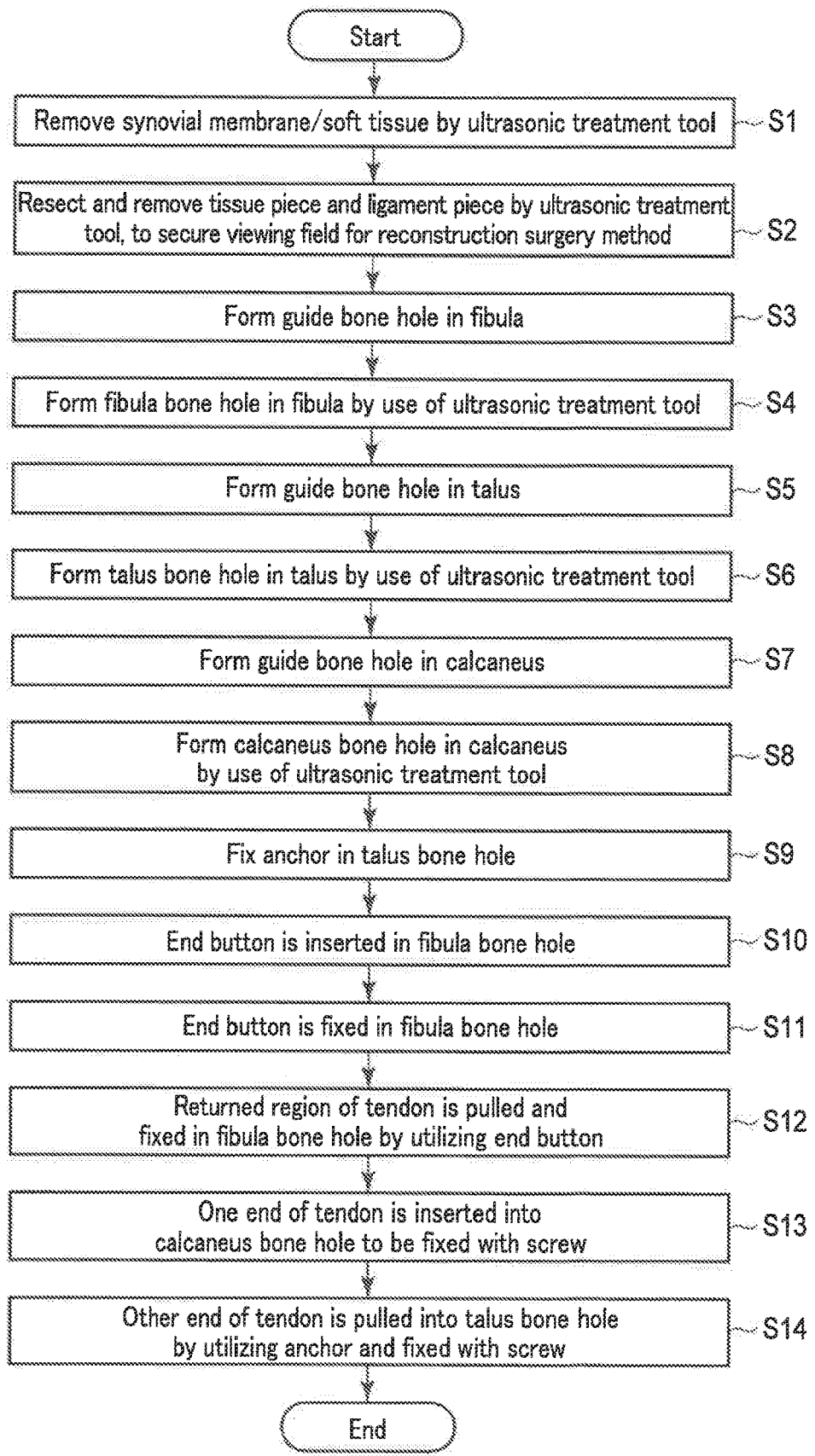
FIG. 6 is a flowchart to explain the arthroscopic surgery method for ankle ligament reconstruction.

Next, the arthroscopic surgery method for ankle ligament reconstruction according to the present embodiment will be described with reference to FIG. 2 and FIG. 6 to FIG. 23. FIG. 6 is a flowchart to explain the arthroscopic surgery method for ankle ligament reconstruction.

Figure 7:
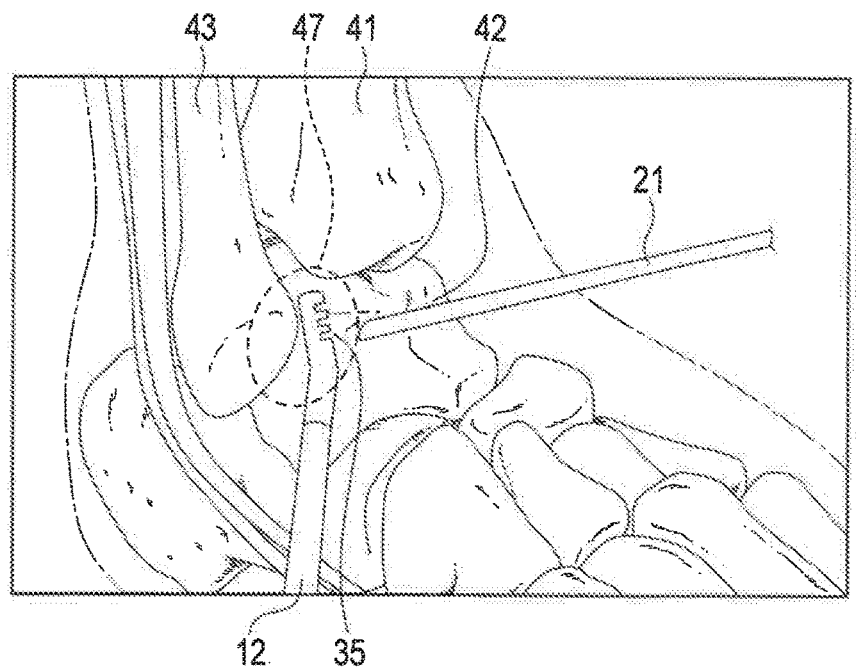
FIG. 7 is a view showing a surgical operation step of sucking and removing a tissue piece or a ligament piece.

First, as shown in FIG. 2, the arthroscope 21 and the probe 12 of the ultrasonic treatment tool which is constituted to be thin and long are inserted through the prepared portals 31 and 32 to remove a synovial membrane/a soft tissue and the like 44 of removal target regions (step S1). In the following drawings, it is defined that the portals are present, but the portals are omitted. Subsequently, as shown in FIG. 7, to secure a viewing field for the reconstruction surgery method, the removal target regions including the synovial membrane, a synovium-related adipose tissue, a persistence ligament 46 and the like are resected by using the ultrasonic treatment tool 2, and tissue pieces or ligament pieces of the region are sucked and removed (step S2). The present embodiment has large advantages obtained by utilizing the ultrasonic treatment tool 2 when removing these removal target regions (the tissue, the ligament, etc.). That is, the ultrasonic treatment tool 2 does not make movement other than the minute vibration, and does not cause damages due to excessive involving and accidental contact as compared with a conventional rotary shaver or the like, and hence even the removal target regions that are very close to a nerve and a blood vessel can safely be removed.

Figure 8:
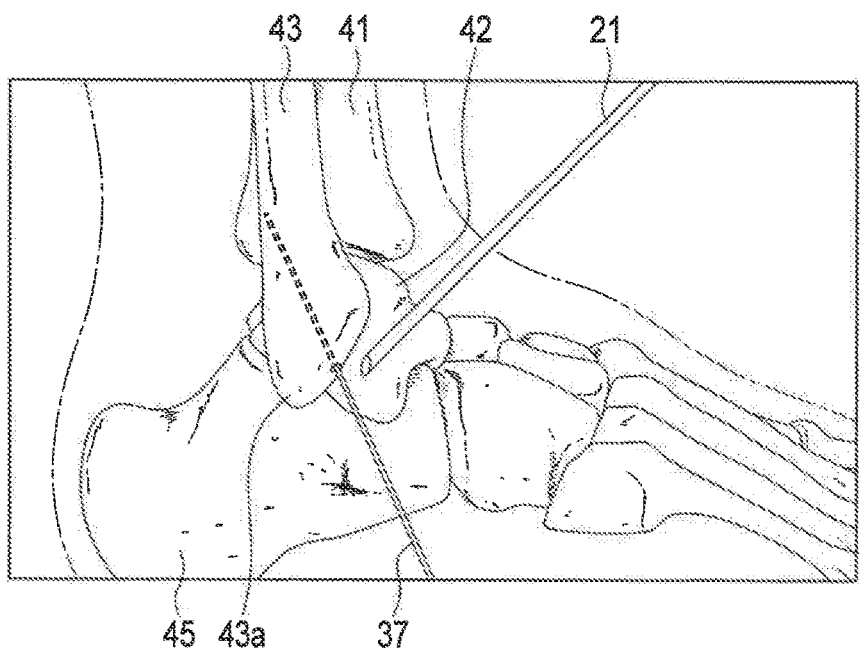
FIG. 8 is a view showing a surgical operation step of forming a guide bone hole in a fibula with Kirschner wire.

Next, as shown in FIG. 8, a Kirschner wire 37 is inserted from a lower part (the vicinity of an ankle) of the fibula 43 to form a guide bone hole 48 (step S3).

Figure 9:
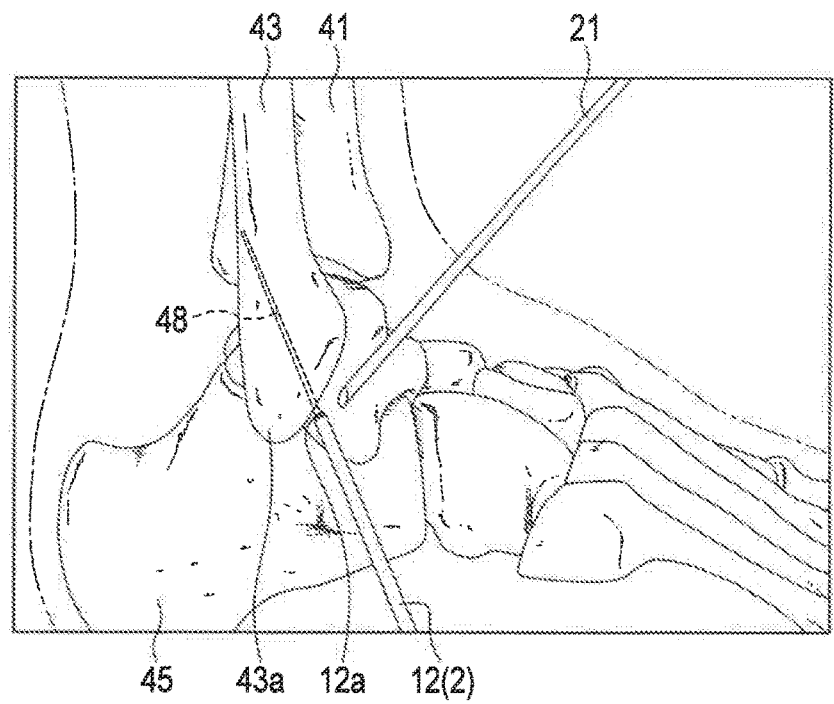
FIG. 9 is a view showing a surgical operation step of forming a fibula bone hole in the fibula.

Next, as shown in FIG. 9, a fibula bone hole 43b is formed in the fibula 43 by use of the probe 12 of the ultrasonic treatment tool 2 comprising treating portion 14 (step S4). At this time, by inserting the pointed projection 14a of the treating portion 14 into the guide bone hole 48, the fibula 43 is cut along the guide bone hole 48 by the ultrasonic vibration. The fibula bone hole 43b has a shape tapered in three stages as described later with reference to FIG. 16. A region of the fibula bone hole 43b which is close to the lower part 43a is formed into an elliptic shape close to a sectional shape of a double folded tendon 66. Needless to say, the shape is not limited to the elliptic shape, and may be a round shape. When this bone hole is prepared, bone pieces and bone powder cut outside are removed from a body by the saline perfused by the water-supply water-discharge section 26.

Figure 10:
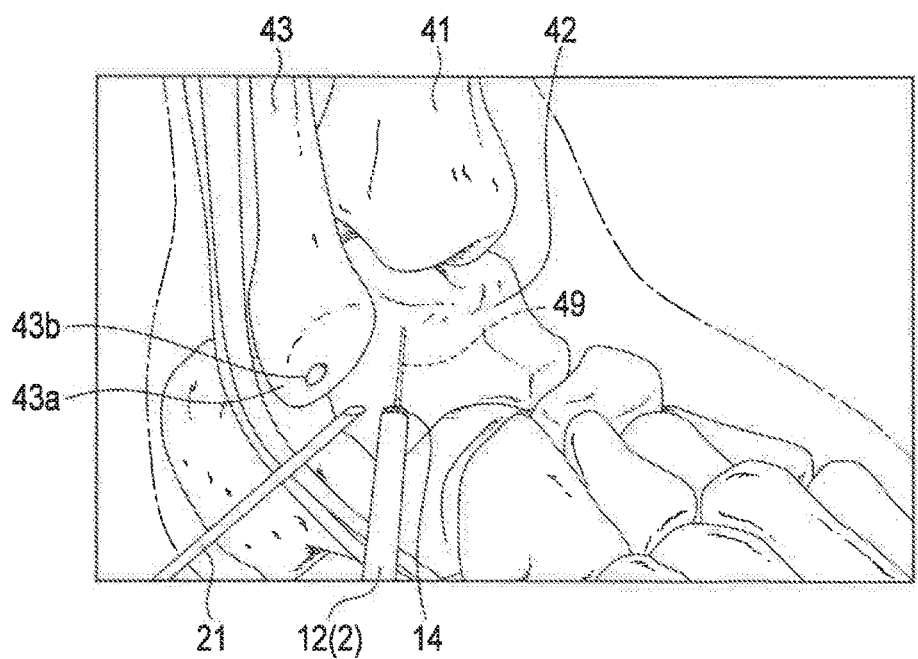
FIG. 10 is a view showing a surgical operation step of forming a guide hole in a talus.
Figure 11:
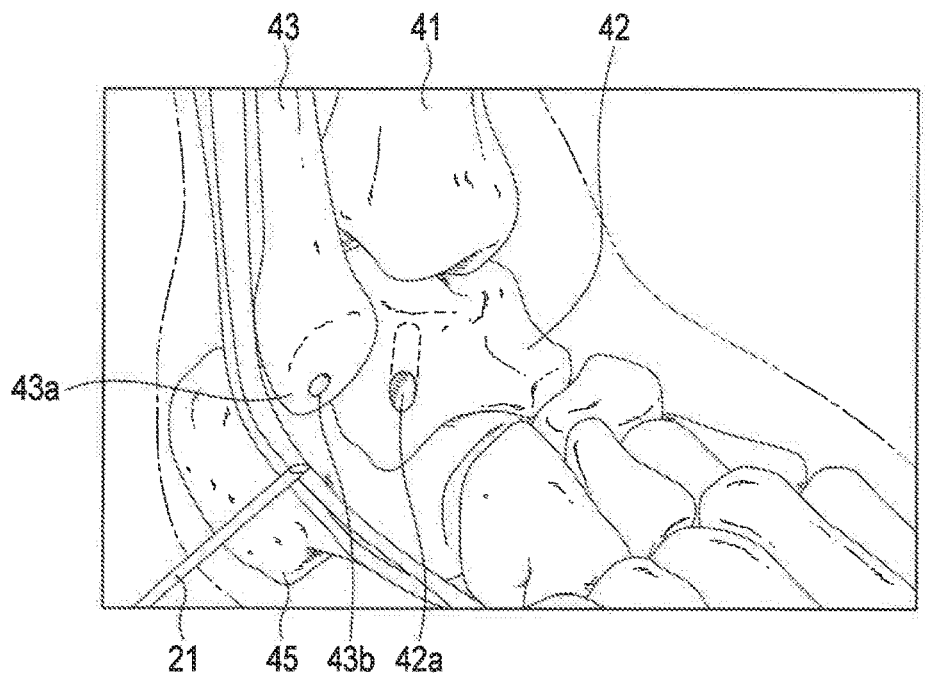
FIG. 11 is a view showing a surgical operation step of forming a talus bone hole in the talus.
Figure 12:
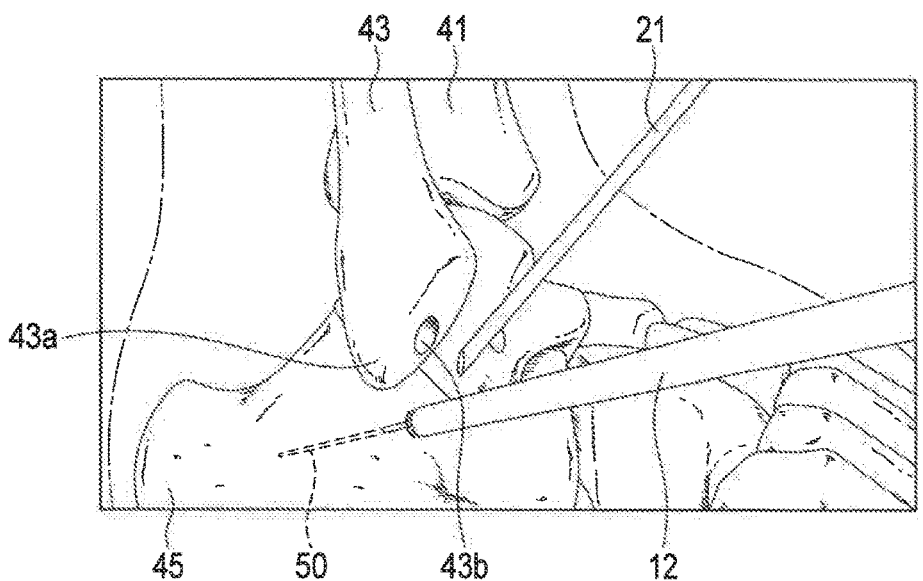
FIG. 12 is a view showing a surgical operation step of forming a guide hole in a calcaneus with the Kirschner wire.
Figure 13:
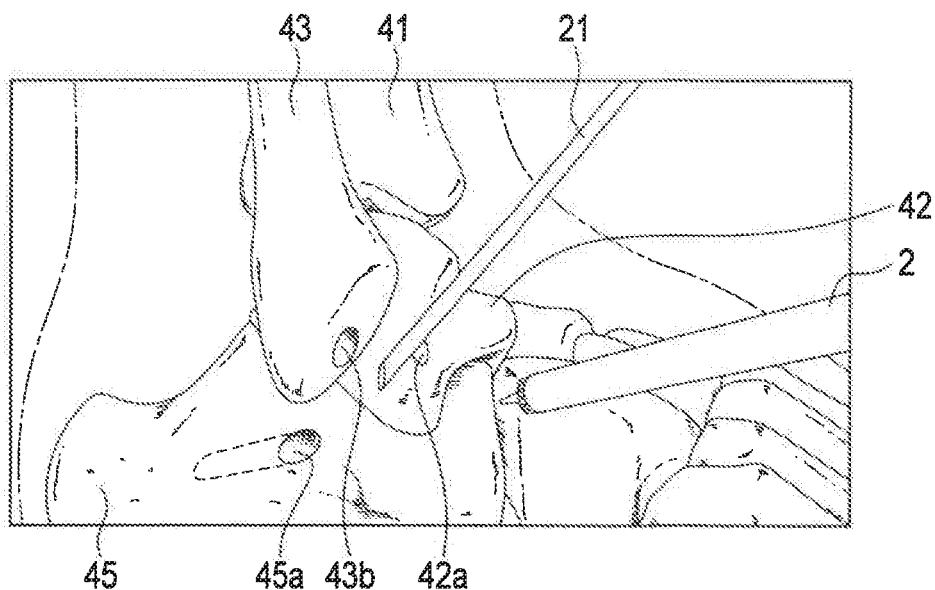
FIG. 13 is a view showing a surgical operation step of forming a calcaneus bone hole in the alcaneus.

Next, similarly as shown in FIG. 10 and FIG. 11, a guide bone bole 49 is formed in the talus 42 (step S5), and then a talus bone hole 42a is formed along the guide bone hole 49 by use of the probe 12 comprising treating portion 14 (step S6). Furthermore, as shown in FIG. 12 and FIG. 13, a guide bone hole 50 is formed in the calcaneus 4542 (step S7), and then a calcaneus bone hole 45a is formed along the guide bone hole 50 by use of the probe 12 comprising the treating portion 14 (step S8).

Figure 14:
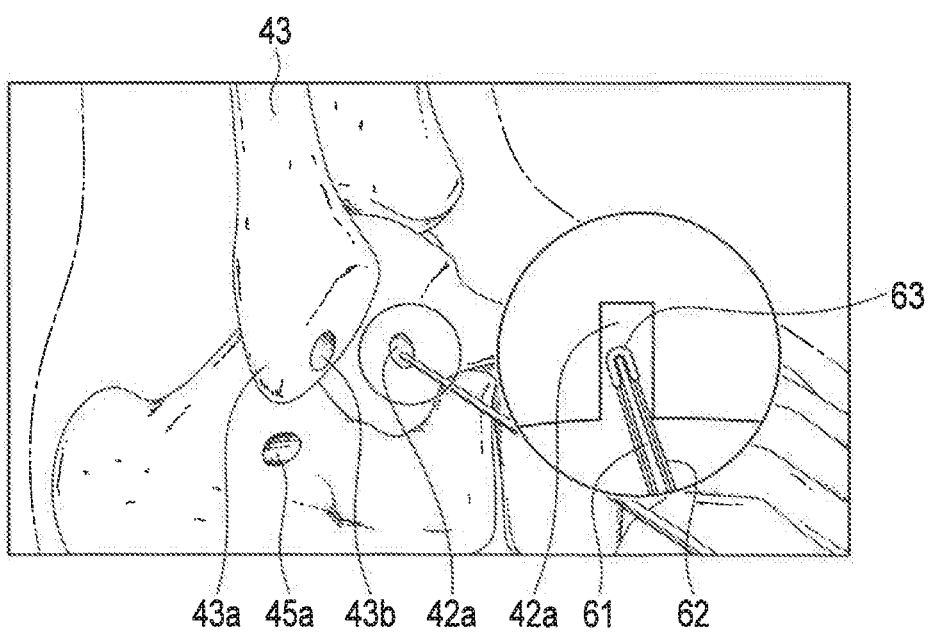
FIG. 14 is a view showing a surgical operation step of attaching, to a fixing jig, an anchor into which a fixing thread is inserted, to place the anchor into the talus bone hole.
Figure 15:
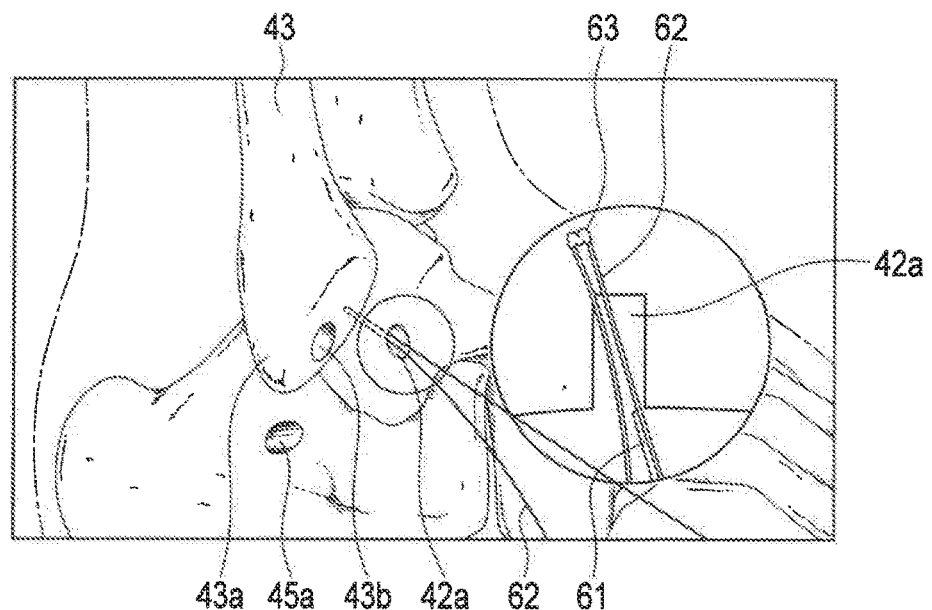
FIG. 15 is a view showing a surgical operation step of fixing the anchor into the talus bone hole.

Next, as shown in FIG. 14, an anchor 63, into which a fixing to thread 62 to support the tendon 66 to be implanted is inserted, is attached to a tip of a handle for exclusive use and placed in the talus bone bole 42a. As shown in FIG. 15, the anchor 63 of the tip is deeply pushed and attached to pierce through an upper bottom of the talus bone hole 42a (step S9). The anchor 63 is fixed in the talus bone hole 42a in a state where the fixing thread 62 is movably inserted into the anchor.

Figure 16:
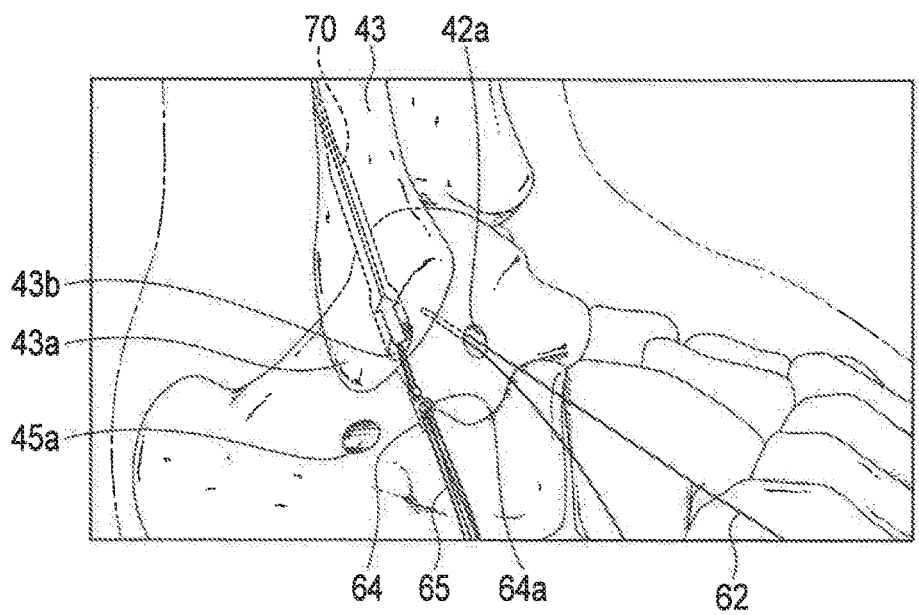
FIG. 16 is a view showing a surgical operation step of pulling an end button into the fibula bone hole.

Next, as shown in FIG. 16, a tip of the fibula bone hole 43b cut from the lower part 43a of the fibula 43 in an oblique direction is extended out through the fibula 43. A fixing thread 70 is fixed by hooking the thread in one hole of an end button 64 made of a metal and pulling the thread out from the tip of the fibula bone hole 43b (step S10) The end button 64 is usually a rectangular metal plate material in which holes are made on both side, and a ring is fixed to a center of the plate material between the two holes. At this time, a traction thread 65 to hold the tendon 66 to be implanted in a pulled state is hooked in the ring of the center of the end button 64.

Figure 17:
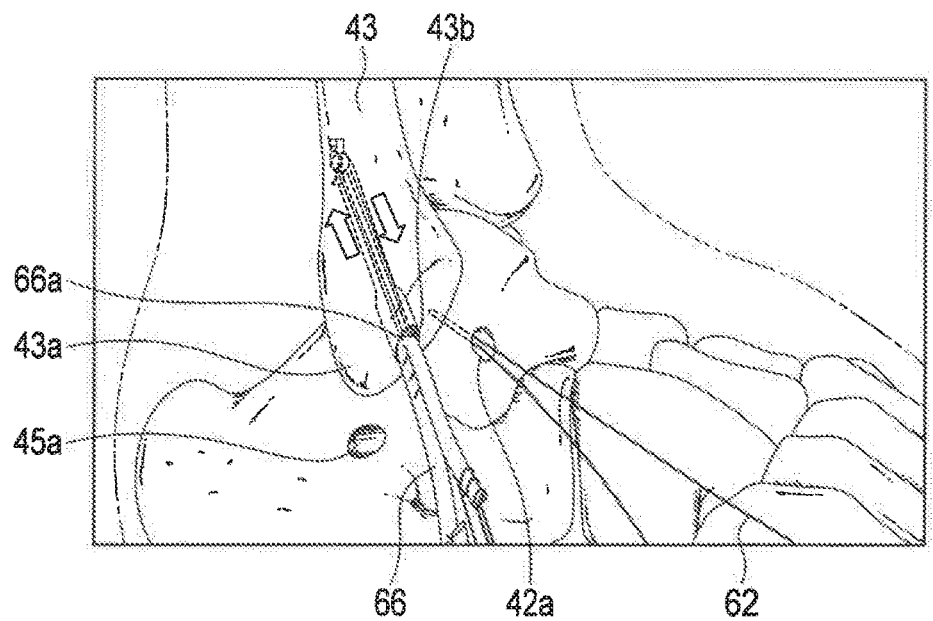
FIG. 17 is a view showing a surgical operation step of pulling up an end button 64 to pull a tendon into the fibula bone hole.

As shown in FIG. 17, the fixing thread 70 is pulled upward to remove the end button 64 from the tip of the fibula bone hole 43b. The end button 64 extended outward is fixed in a configuration in which the plate member sticks to the outside to close the fibula bone hole 43b and the ring of the center remains in the fibula bone hole 43b (step S11).

Figure 18:
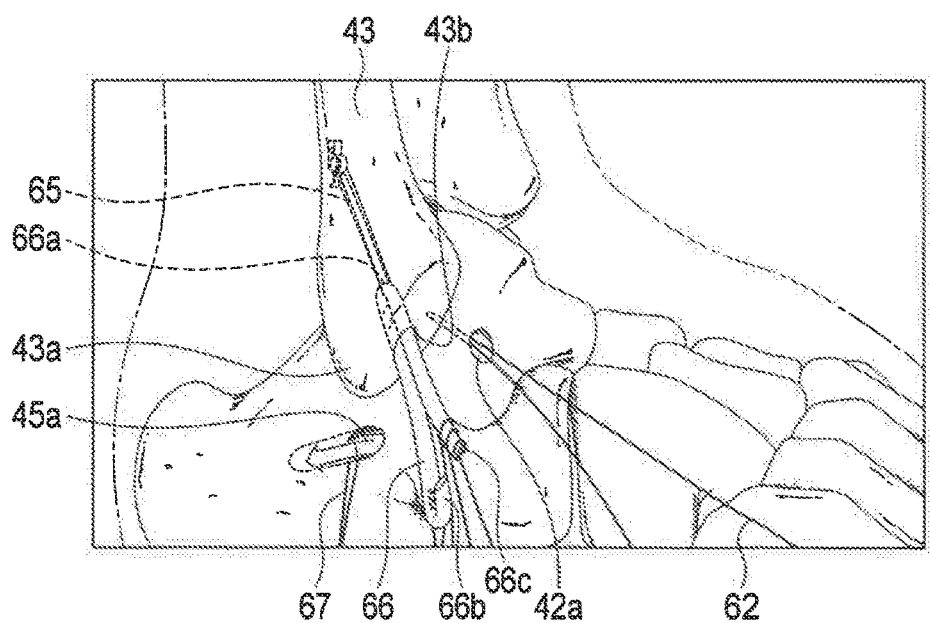
FIG. 18 is a view showing a surgical operation step of fixing a folded region of the tendon into the fibula bone hole to fix the region with a traction thread.

As shown in FIG. 18, one end of the traction thread 65 is coupled to be sewn on a folded region 66a of the double folded tendon 66, the other end of the traction ad 65 is pulled toward to the operator to pull a part of the folded region of the tendon 66 into the fibula bone hole 43b through the ring of the end button 64 as shown in FIG. 18, and the tendon 66 is fixed by fixing the traction thread 65 in a state where the part of the folded region is pulled inside (step S12). Furthermore, one end 66b of the double folded tendon 66 is returned to sew the one end with a fixing thread 67, and another end 66c is tied with the fixing thread 62.

Figure 19:
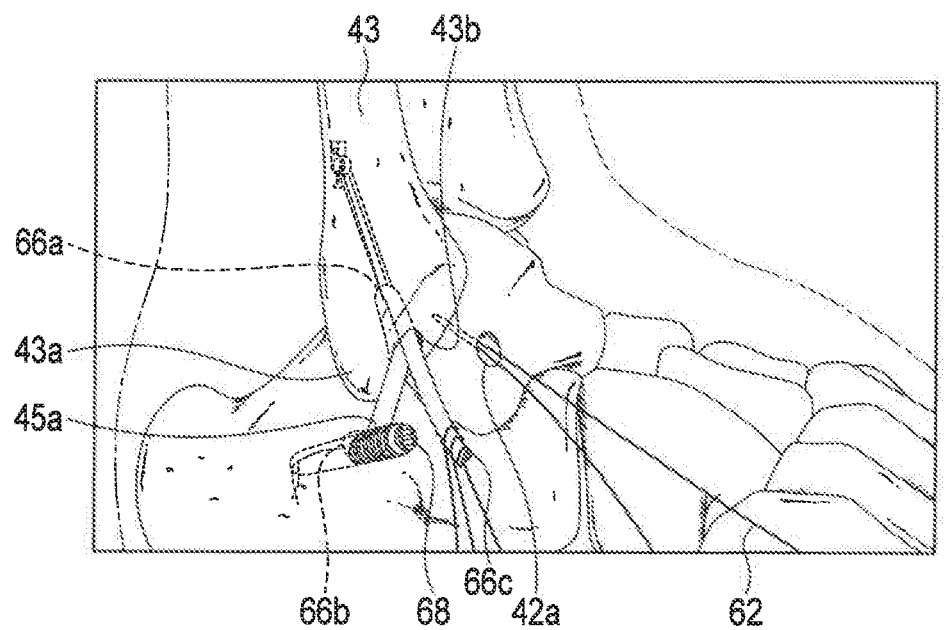
FIG. 19 is view showing a surgical operation step of fixing the tendon to the fibula bone hole with a screw.

The fixing thread 67 is inserted into the calcaneus bone, hole 45a, and subsequently, as shown in FIG. 19, the other end 66b of the tendon 66 is also inserted into the calcaneus bone hole, whereby the tendon is fixed by a fixing anchor 68 (step S13).

Figure 20:
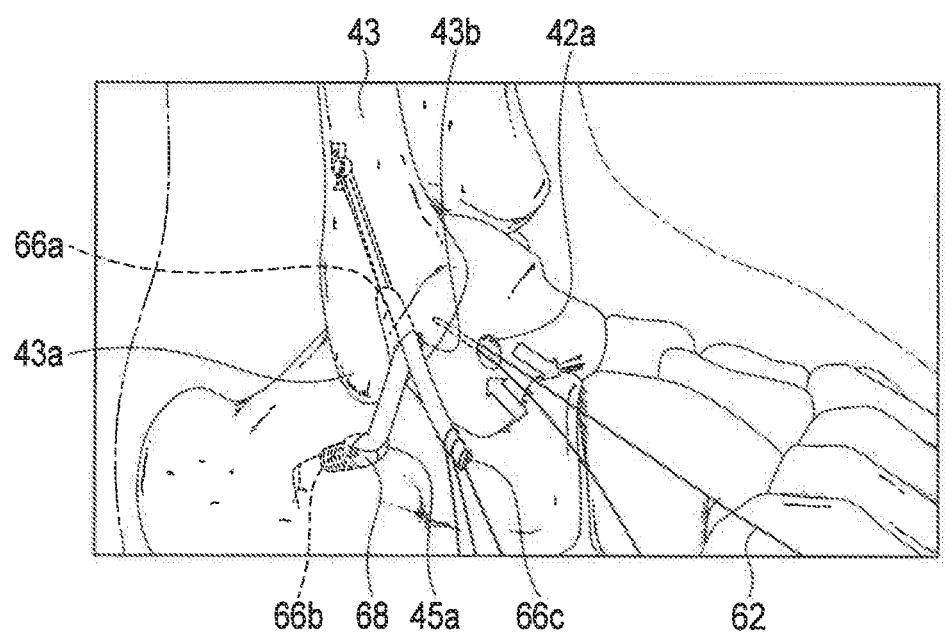
FIG. 20 is a view showing a surgical operation step of pulling the tendon into the talus bone hole.

Next, as shown in FIG. 20, the fixing thread 62 is pulled via the anchor 63 fixed in the talus bone hole 42a and the one end 66c of the tendon 66 is pulled into the talus bone hole 42a. Afterward, as shown in FIG. 21, a screw 69 is fixed to push the one end 66c of the tendon 66 into the talus bone hole 42a (step S14). The tendon 66 is fixed to apply predetermined tension to each of a region between the fibula bone hole 43b and the talus bone hole 42a and a region between the fibula bone hole 43b and the calcaneus bone hole 45a. According to the above-mentioned procedure, by use of the ultrasonic treatment tool under the arthroscope of the present embodiment, the ankle ligament can be reconstructed.

The ultrasonic treatment tool of the present embodiment mentioned above has the following operations and effects.

The distal portion of the ultrasonic treatment tool does not rotate, but minutely vibrates to perform the cutting, so that the cutting treatment can safely be carried out without involving any peripheral tissues of the treatment target.

The shape of the bone hole formed by using the ultrasonic treatment tool is not limited to a linear round shape as in the drill, and the bone hole can be formed into each of a linear shape and a curved shape in a depth direction. Additionally, a laterally sectional shape of the bone hole is not limited to the round shape, and the hole can be formed into the desirable shape by moving the treating portion during the cutting. Additionally, by using the treating portion beforehand formed in a desirable shape such as the round shape, an elliptic shape, a long hole shape or a rectangular shape, the hole can be formed into the desirable shape without moving the treating portion.

Additionally, it is also possible to form the bone hole into the shape corresponding to the sectional shape of the tendon (the ligament) removed from the other region for use in the reconstruction at once. Additionally, the treating portion may beforehand be prepared into a shape equal to the sectional shape of the tendon.

By the ultrasonic treatment tool, both the soft tissue and a hard tissue can be treated, and hence the tissues can be treated by the same treatment tool though a conventional treatment tool has to be replaced in accordance with a treatment target region, so that the ultrasonic treatment tool is efficient, and is capable of shortening a surgical operation time and decreasing burdens on a patient.

The ultrasonic treatment tool performs a treatment of cutting the treatment target region by the ultrasonic vibration without heating the treatment target region, and hence thermal damages can be decreased, postoperative progress can suitably be obtained and the ultrasonic treatment tool is excellent in less invasive properties.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A method of forming a hole for fixing a tendon to a bone, the method using a drill and an ultrasonic treatment device with a flat treating portion, the method comprising:
   forming a circular guide hole in the bone by the drill;
   placing a distal end of the treating portion at the guide hole; and
   moving the distal end of the treating portion along the guide hole while ultrasonically vibrating the treating portion, so that a quadrilateral hole that is larger than the guide hole is formed in the bone,
   wherein:
      the ultrasonic treatment device comprises a distal part and a proximal part in a direction of a longitudinal axis, and is configured to transmit ultrasonic vibration;

the ultrasonic treatment device comprises the treating portion at the distal part, and the distal end of the treating portion has a quadrilateral projected shape when viewed from a direction of the distal part toward the proximal part; and the treating portion includes a treating surface that includes a first portion and a plurality of second portions, a distal-most surface of the plurality of second portions each including a sharp edge configured to cut bone and being closer to the proximal part than a distal-most surface of the first portion.

2. The method according to claim 1, wherein surfaces on which the plurality of second portions are located are symmetrical with respect to a surface on which the first portion is located when viewed from the direction of the distal part toward the proximal part.

3. The method according to claim 1, wherein the first portion and the plurality of second surfaces are provided on the treatment surface such that the first portion is disposed at a center region of the treatment surface.

4. The method according to claim 1, wherein:
the treating portion includes a first tier, a second tier, and a third tier;
the first tier includes a flat surface of the treatment portion that does not include the first portion and the second portion;
the second tier includes the plurality of second portions; and
the third tier includes the first portion.

5. The method according to claim 1, further comprising a third portion provided closer to the proximal part than the first portion and the plurality of second portions.

\* \* \* \* \*